United States Patent [19]

Triunfol

[11] Patent Number: 4,488,544
[45] Date of Patent: Dec. 18, 1984

[54] BODY RESTRAINT FOR INVALID PATIENTS AND THE LIKE

[76] Inventor: David Triunfol, 2001 N. 72 Ct., Elmwood Park, Ill. 60635

[21] Appl. No.: 450,073

[22] Filed: Dec. 15, 1982

[51] Int. Cl.³ .............................................. A61F 13/00
[52] U.S. Cl. ................................... 128/134; 2/DIG. 7
[58] Field of Search ............ 128/134, 133; 2/DIG. 7, 2/73

[56] References Cited

U.S. PATENT DOCUMENTS

| | | | |
|---|---|---|---|
| 2,751,594 | 6/1956 | Brissenden | 128/134 X |
| 2,851,033 | 9/1958 | Posey | |
| 3,136,311 | 6/1964 | Lewis | 128/134 |
| 3,137,294 | 6/1964 | Robertson | 128/134 |
| 3,181,530 | 5/1965 | Storey | 128/134 |
| 3,265,065 | 8/1966 | Jillson | 128/134 |
| 3,276,431 | 10/1966 | Murcott | |
| 3,276,432 | 10/1966 | Murcott | |
| 4,050,737 | 9/1977 | Jordan | |
| 4,117,840 | 10/1978 | Rasure | 128/134 |
| 4,119,095 | 10/1978 | Lewis | 128/134 |

*Primary Examiner*—Stephen C. Pellegrino
*Attorney, Agent, or Firm*—Andrus, Sceales, Starke & Sawall

[57] ABSTRACT

A wrap around patient restraint includes a unitary vest body having a front panel and a pair of separable back panels having vertical edge portions which are normally adapted to overlap. The vest body also has a lower horizontal edge portion at approximately waist level. The inner and outer overlapping vertical edge portions of the back panels are respectively provided with attached reinforcing straps, with their attachment to the vest body terminating at the top of the panels adjacent the neck portion. The outer strap extends beyond the attachment terminus to form a first elongated free end for attachment to a bed or the back of a wheelchair. A horizontal slot is disposed in the vest body above the terminus of the outer strap attachment. The inner strap also extends beyond its attachment terminus to form a second elongated free end which passes outwardly through the horizontal slot. The lower horizontal edge portion of the vest body is provided with an attached waist encircling reinforcing strap. The attachment terminates at the overlapping lower corners of the back panels and each end of the strap thereupon extends freely from its respective corner. The strap extending from the inner lower corner of one back panel passes outwardly through a vertical slot disposed in the opposite back panel, while the strap extending in the opposite direction from the outer lower corner of the other back panel passes through a loop in the respective opposite back panel. The vertical slot passes through the material of the vest body itself and also the waist encircling reinforcing strap, and is partially offset upwardly from the plane of the latter. The free ends of the waist encircling strap are adapted for attachment to the bedframe of a bed or the arm portions of a wheelchair.

6 Claims, 5 Drawing Figures

U.S. Patent  Dec. 18, 1984  4,488,544
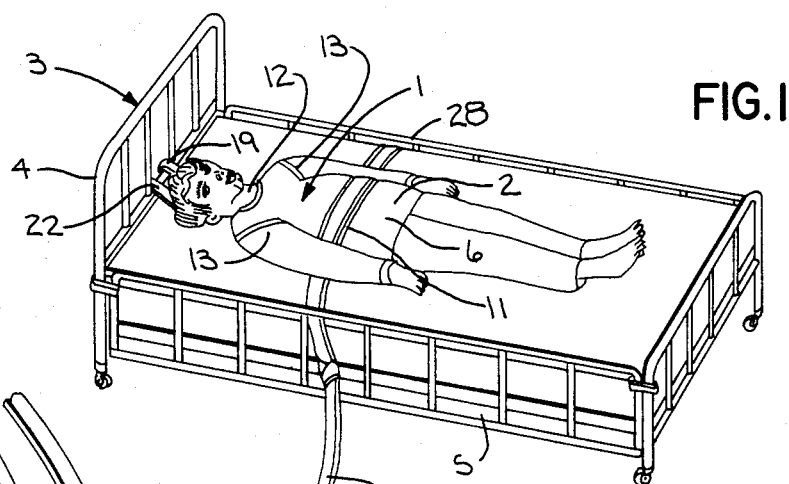
FIG.1
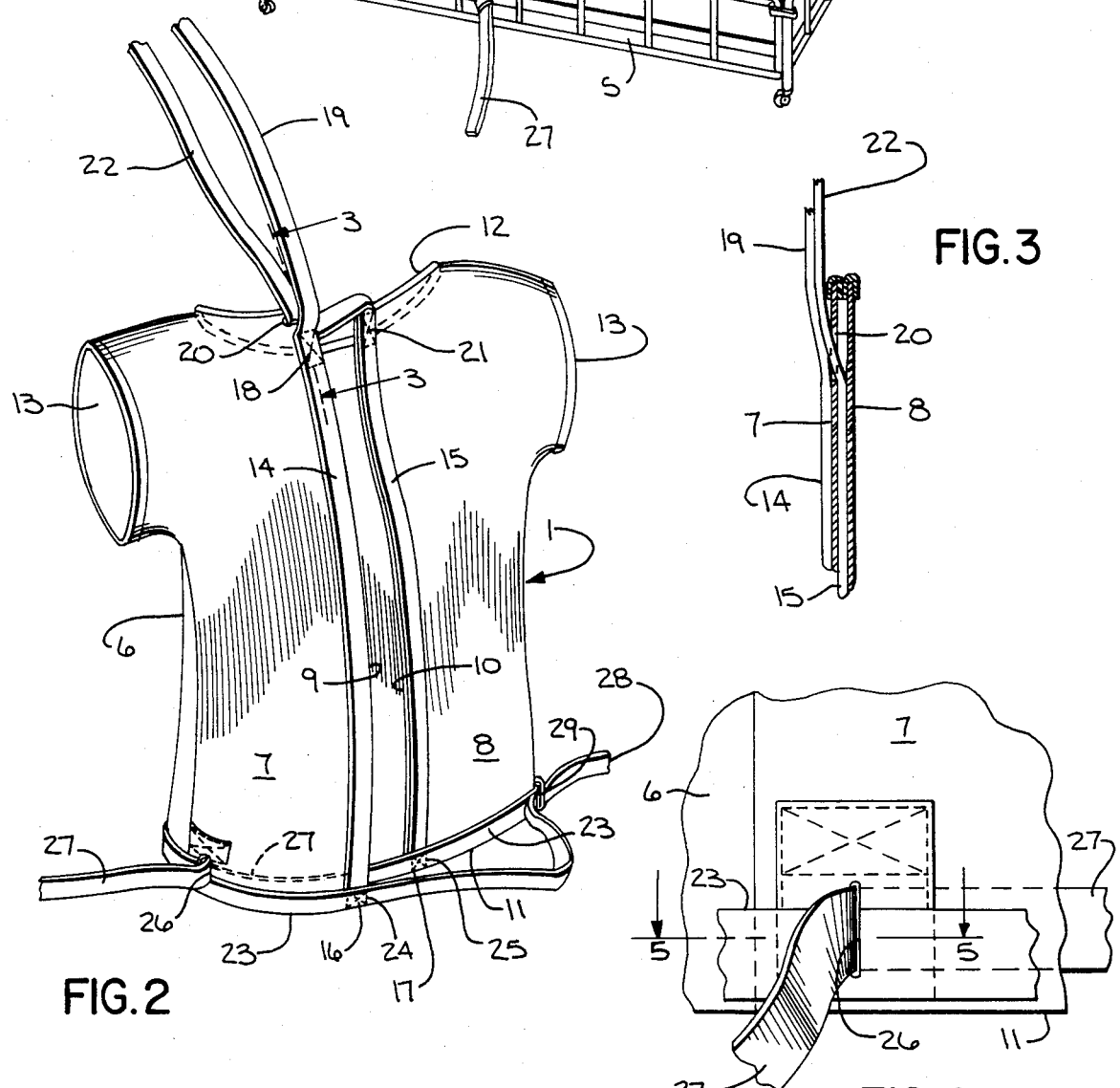
FIG.2
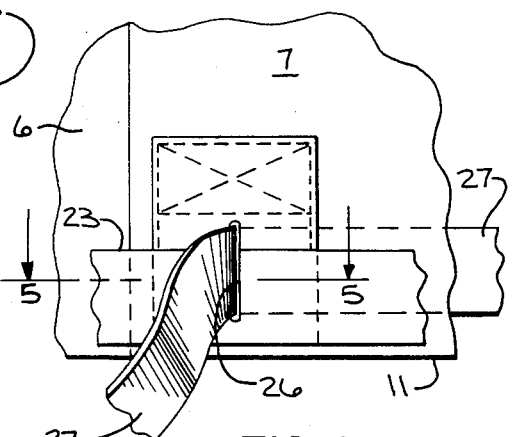
FIG.3
FIG.4
FIG.5
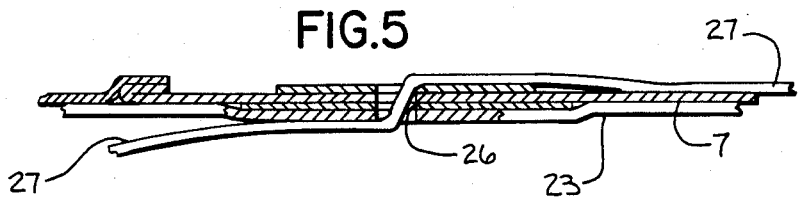

BODY RESTRAINT FOR INVALID PATIENTS AND THE LIKE

U.S. PRIOR ART OF INTEREST

U.S. Pat. Nos. 2,851,033, Posey, Sep. 9, 1958: 3,136,311, Lewis, June 9, 1964: 3,181,530, Storey, May 4, 1965: 3,276,431, Murcott, Oct. 4, 1966: 3,276,432, Murcott, Oct. 4, 1966: 4,050,737, Jordan, Sep. 27, 1977.

BACKGROUND AND SUMMARY OF THE INVENTION

This invention relates to a body restraint for invalid patients and the like.

Body restraints are known which wrap around a patient's torso and which are provided with a strap only at waist level which can be secured to a bed or chair. It has been found that patients can sometimes release themselves from such restraints, as by struggling to get the shoulder portion off, which then permits the restraint to slide down the body over the legs.

At least some of the above-identified patents disclose body restraint devices which make it more difficult for a patient to struggle out of them. These devices usually have included some sort of further strap or holding device at shoulder level. However, many of these restraints are cumbersome and complex to manipulate, are subject to tangling or twisting, and are relatively expensive to manufacture. Furthermore, some of them rely on metal fasteners or the like, which can be a danger to the patient. In addition, some do not permit the patient to turn or be turned when in bed.

It is an object of the present invention to provide an improved body restraint which is not subject to the above disadvantages, and which is simple to apply to the patient, yet firmly holds the patient against undesirale release.

In accordance with the various aspects of the invention, a wrap around patient restraint is provided which includes a unitary vest body having a front panel and a pair of separable back panels having vertical edge portions which are normally adapted to overlap. The vest body also has a lower horizontal edge portion at approximately waist level.

The inner and outer overlapping vertical edge portions of the back panels are respectively provided with attached reinforcing straps, with their attachment to the vest body terminating at the top of the panels adjacent the neck portion. The outer strap extends beyond the attachment terminus to form a first elongated free end for attachment to a bed or the back of a wheelchair. A horizontal slot is disposed in the vest body above the terminus of the outer strap attachment. The inner strap also extends beyond its attachment terminus to form a second elongated free end which passes outwardly through the horizontal slot.

Likewise, the lower horizontal edge portion of the vest body is provided with an attached waist encircling reinforcing strap. The attachment terminates at the overlapping lower corners of the back panels and each end of the strap thereupon extends freely from its respective corner. The strap extending from the inner lower corner of one back panel passes outwardly through a vertical slot disposed in the opposite back panel, while the strap extending in the opposite direction from the outer lower corner of the other back panel passes through a loop in the respective opposite back panel. The vertical slot passes through the material of the vest body itself and also the waist encircling reinforcing strap, and is partially offset upwardly from the plane of the latter. The free ends of the waist encircling strap are adapted for attachment to the bedframe of a bed or the arm portions of a wheelchair.

BRIEF DESCRIPTION OF THE DRAWINGS

The accompanying drawings illustrate the best mode presently contemplated by the inventor for carrying out the invention.

In the drawings:

FIG. 1 is a view of a patient lying in bed and wearing the body restraint of the invention;

FIG. 2 is an enlarged rear perspective view showing the restraint applied to a person with the outer back panel spaced from the inner panel prior to tightening, for purposes of clarity of illustration;

FIG. 3 is a vertical section taken on line 3—3 of FIG. 2 and with the body restraint pulled tight;

FIG. 4 is a fragmentary plan view of the vertical slot area; and

FIG. 5 is a horizontal section taken on line 5—5 of FIG. 4 and with the body restraint pulled tight.

DESCRIPTION OF THE PREFERRED EMBODIMENT

As shownin the drawings, the invention is directed to a body restraint 1 for a patient 2 who needs to be held tightly in, for example, a wheelchair (not shown) or a bed 3 including a head 4 and bedframe 5.

Restraint 1 may be made of any suitable material such as strong cloth and comprises a generally unitary wrap around vest body having a front panel 6 which merges rearwardly into a pair of left and right back panels 7 and 8 having respective generally vertical edge portions 9 and 10 which in use are adapted to normally overlap centrally of the back. As shown, outer edge portion 9 extends over inner edge portion 10 so that the respective back panels 7 and 8 will be designated "outer" and "inner" also.

The restraint body also includes a lower horizontal edge or waist portion 11, and generally forms a neck opening 12 and arm openings 13.

Referring particularly to FIGS. 2 and 3, outer and inner edge portions 9 and 10 are provided with respective generally vertical co-extensive outer and inner reinforcing straps 14 and 15. The straps are attached to the restraint material, as by sewing or the like. In the illustrated embodiment, the attached straps 14 and 15 extend from the overlapping back panel corners 16 and 17 and up along edge portions 9 and 10 where the attachment terminates adjacent neck opening 12.

Outer strap 14 extends beyond its upper attachment terminus 18 to form a first elongated free end 19 which can be suitably tied to bed head 4 or the like.

A horizontal slot 20 is disposed in outer back panel 7 just upwardly from the upper attachment terminus 18 of outer strap 14. Inner strap 15 also extends beyond its attachment terminus 21, which is positioned generally beneath slot 20. The free end 22 of strap 15 extends upwardly through slot 20 for tying to bed head 4 or the like.

The lines of departure of free ends 19 and 22 from restraint 1 are confined to a closely restricted area, which assists in reinforcement of the neck area against tearing or ripping.

Referring now to FIGS. 2, 4 and 5, the lower horizontal waist portion 11 of restraint 1 is provided with a generally co-extensive waist encircling reinforcing strap 23 which also is attached to the restraint material as by sewing. An attachment terminus for strap 23 is disposed at outer corner 16, as at 24, and at inner corner 17, as at 25.

A vertical slot 26 is positioned in substantially spaced horizontal relationship from corner 16 in outer back panel 7 and passes through both the restraint body material and waist strap 23. To prevent slot 26 from breaking through to the very lower edge of the restraint, when placed under tension, slot 26 is partially offset upwardly from the plane of strap 23, as shown in FIG. 4, thereby increasing the amount of dual-strata material between the lower slot end and the garment edge.

One end of waist strap 23 extends beyond inner terminus 25 to form a free end 27 which extends horizontally beneath outer back panel 7 and upwardly through slot 26 for tying to a bed siderail 5 or the like. The other end of waist strap 23 extends beyond outer terminus 24 to form a second free end 28 which extends in the opposite direction from free end 27 and horizontally over inner back panel 8, and hence through a loop 29 mounted to the latter. Free end 28 hence can be tied to the opposite bedframe portion 5 or the like.

The combined slot and loop arrangement at waist level assists in keeping the waist strap ends in place and relatively free of twisting.

It is to be noted that slots 20 and 26 are both disposed in one of the back panels, namely panel 7. Furthermore, attachment terminus 21 for vertical strap 15 and inner attachment terminus 25 for horizontal strap 23 are both disposed in the other back panel, namely panel 8. The free end extensions of both straps thus extend from one panel and are threaded outwardly through the respective slots to hold the back panels in proper relative position.

The restraint of the invention provides an improvement over prior known restraints. The restraint cannot easily be removed by the patient, yet is simple to apply and relatively inexpensive to manufacture. The device requires no buttons or clamps which could be hazardous to the patient, and readily permits turning by the patient while in a reclining or upright position in bed.

Although outer back panel 7 is shown as the left panel and inner back panel 8 is shown as the right panel, the positions thereof could be reversed without departing from the spirit of the invention.

Various modes of carrying out the invention are contemplated as being within the scope of the following claims particularly pointing out and distinctly claiming the subject matter which is regarded as the invention.

I claim:

1. A wrap around restraint for invalid patients and the like, comprising, in combination:
   (a) a generally unitary vest body having a front panel which merges rearwardly into outer and inner back panels which normally overlap along generally vertical outer and inner edge portions respectively,
   (b) said front and back panels forming a lower horizontal edge portion at the waist of the vest body,
   (c) first and second reinforcing straps attached to said inner back panel at the upper end of said inner vertical edge portion and on the horizontal edge portion thereof, respectively, and with each said strap having an attachment terminus with a free strap end extending beyond said terminus,
   (d) and slots disposed in said outer back panel at the upper end of said outer vertical edge portion and on the horizontal edge portion thereof for threadably receiving the respective said free strap ends from beneath and outwardly therethrough for attachment to a bed or the like.

2. The wrap around restraint of claim 1:
   (a) which includes a third reinforcing strap attached to said outer back panel,
   (b) said third strap having an attachment terminus disposed adjacent and below the slot in said outer back panel with a free strap end extending beyond said last-named terminus,
   (c) the said straps on said outer and inner back panels extending generally vertically along said outer and inner edge portions respectively and being generally co-extensive.

3. The wrap around restraint of claim 1:
   (a) wherein said second reinforcing strap is generally co-extensive with the said horizontal edge portion of said vest body to encircle the waist of the patient,
   (b) said second strap also having an attachment terminus on the horizontal edge portion of said outer back panel with a free strap end extending beyond said last-named terminus,
   (c) and a loop in the horizontal edge portion of said inner back panel for receiving said last-named free strap end therethrough.

4. The wrap around restraint of claim 1:
   (a) which includes a third reinforcing strap attached to said outer back panel,
   (b) said third strap having an attachment terminus disposed adjacent and below the slot in said outer back panel with a free strap end extending beyond said last-named terminus,
   (c) the said straps on said outer and inner back panels extending generally vertically along said outer and inner edge portions respectively and being generally co-extensive,
   (d) said second reinforcing strap being generally co-extensive with the said horizontal edge portion of said vest body to encircle the waist of the patient,
   (e) said second strap also having an attachment terminus on the horizontal edge portion of said outer back panel with a free strap end extending beyond said last-named terminus,
   (f) and a loop in the horizontal edge portion of said inner back panel for receiving said last-named free strap end therethrough.

5. The wrap around restraint of claim 1 wherein:
   (a) said slot in said vertical edge portion extends horizontally,
   (b) and said slot in said horizontal edge portion extends vertically and passes through and is partially offset upwardly from said second strap.

6. The wrap around restraint of claim 4 wherein:
   (a) said slot in said vertical edge portion extends horizontally,
   (b) and said slot in said horizontal edge portion extends vertically and passes through and is partially offset upwardly from said second strap.

* * * * *